US005893361A

United States Patent [19]
Hughes

[11] Patent Number: 5,893,361
[45] Date of Patent: Apr. 13, 1999

[54] ACOUSTIC TRANSCEIVER RESPIRATORY THERAPY APPARATUS AND METHOD

[76] Inventor: Arthur R. Hughes, 2736 S. Uravan, Aurora, Colo. 80013

[21] Appl. No.: 09/096,878

[22] Filed: Jun. 12, 1998

Related U.S. Application Data

[63] Continuation of application No. 08/843,745, Apr. 21, 1997.
[51] Int. Cl.$^6$ ............................................. A61M 15/00
[52] U.S. Cl. ............................. 128/200.24; 128/204.18
[58] Field of Search ..................... 128/200.24, 202.16, 128/202.28, 202.29, 204.18, 204.25; 482/13

[56] References Cited

U.S. PATENT DOCUMENTS

| | | | |
|---|---|---|---|
| 2,918,917 | 12/1959 | Emerson | 128/204.18 |
| 4,054,134 | 10/1977 | Kritzer | 482/13 |
| 4,813,403 | 3/1989 | Endo | 128/32 |
| 5,018,517 | 5/1991 | Liardet | 482/13 |
| 5,193,529 | 3/1993 | Labaere | 482/13 |
| 5,451,190 | 9/1995 | Liardet | 482/13 |
| 5,569,122 | 10/1996 | Cegla | 482/13 |

OTHER PUBLICATIONS

General Physiotherapy, Inc., *Flimm Fighter*™ Operating Instruction Manual, 1993.
American Biosystems, *The ThAIRaphy*™ Vest Clearance System, Dec. 1995.
Med Systems, *Meds Model 2500 Fluid Flo Percussor*, Jan. 1995.

*Primary Examiner*—Aaron J. Lewis
*Attorney, Agent, or Firm*—John R. Wahl; Holland & Hart LLP

[57] ABSTRACT

An active respiratory therapeutic device and method for actively loosening and breaking up mucus plugs and phlegm in a user's trachea and bronchial passages and lungs while a user is breathing normally through the device comprises a housing containing a base portion and a cap portion forming at least a portion of a sonic coupling chamber adapted to be held in a patient's mouth during normal breathing activity. The cap portion also includes breathing passages out of the chamber so that the user can breath normally through device during operation. The base portion contains an acoustic generator behind a sanitary flexible diaphragm separating the portions. The acoustic generator produces an audio waveform which may be controlled by the user or automatically controlled by a feedback signal to optimize a sensed parameter indicative of the user's breathing efficiency such as the sound of the user's exhaled breath, blood oxygen levels, or ultrasonic signature changes of mucus plugs. This feedback signal senses a patient parameter and automatically adjust the operating frequency spectrum and/or pulse rate of the device to optimally affect the monitored parameter such as the user's breathing efficiency. The method of the invention basically comprises determining a resonant frequency of a mucus plug, generating an acoustic waveform including the resonant frequency and directing the waveform into a user's airways to loosen the plug while the user breathes through his or her airways.

32 Claims, 4 Drawing Sheets

ACOUSTIC TRANSCEIVER RESPIRATORY THERAPY APPARATUS AND METHOD

CROSS REFERENCE TO RELATED APPLICATION

This application is a continuation in part of U.S. patent application Ser. No. 08/843,745, filed Apr. 21, 1997 entitled ACOUSTIC RESPIRATORY THERAPY APPARATUS.

BACKGROUND OF THE INVENTION

1. Field of the Invention

This invention generally relates to respiratory devices and more particularly to a vibrating device and method which assists in breaking up and dislodging accumulated fluids and solids generated in a user's lungs.

2. Description of the Related Art

People who have lung diseases such as cystic fibrosis, bronchiactasis and chronic bronchitis have a difficult time breaking up, dislodging, and expelling mucus and phlegm which develops in the lungs. The presence of this material in the lungs and bronchial and tracheal passages provides an excellent media for growth of bacteria. For treatment of the condition, rotation of antibiotics is used to treat the bacterial infections that result. Postural drainage with induced vibration , percussive therapy and/or the use of a mechanical device such as a flutter valve are often used to help the patient dislodge this mucus material.

Such percussive devices are disclosed in U.S. Pat. Nos. 5,018,517 and 5,451,190 to Liardet. This device is self powered, as are other flutter valve devices available and in use today. That is, the patient exhales into the device which sets up vibrations which feed back through the patient's air ways to break up and dislodge the phlegm. However, this activity is energy consumptive and very draining to the patient. Often, because of a debilitating condition from the effects of pneumonia, for example, the patient has great difficulty blowing into these self powered mechanical devices with sufficient force to achieve any substantive success at dislodging accumulated phlegm.

An active vibratory device is disclosed in U.S. Pat. No. 4,813,403 to Endo. This device comprises an oscillator for generating an electrical signal at a frequency optimally effective for the patient, an audio amplifier, and a transducer connected, through a closed gas volume, to a vibratory diaphragm which is placed against the patient's body, typically the patient's chest or back. The vibration is then transferred from the transducer, through the closed gas volume, to the diaphragm, then to the surface of the patient's body to treat such problems as shoulder discomfort, arthritis, asthmatic spasms and improve blood circulation. The major disadvantage with this approach when the lungs are the target is that by placing the unit on a user's back or chest, the intervening body tissue may substantially attenuate the vibration before it reaches the target area of the lungs and bronchial tubes.

Therefore there is an urgent need for a device that can efficiently and effectively transmit acoustic vibrations to the sites of phlegm buildup in the patient's lungs. There is also a need for a device which does not exhaust the patient's energy during device operation so that this energy can be reserved for effective expulsion of dislodged phlegm.

SUMMARY OF THE INVENTION

The method and apparatus in accordance with the present invention meets the above identified needs.

It is thus an object of the invention to provide a powered apparatus for directly assisting a patient in breaking up phlegm and mucus plugs in the patient's lungs and bronchial tubes.

It is another object of the invention to provide a powered acoustical apparatus that the patient may adjust to achieve optimal breakup of phlegm and mucus plugs.

It is another object of the invention to provide a powered acoustical apparatus that a patient may utilize to achieve optimal breakup of phlegm and mucus plugs without generating bothersome sound levels to persons in close proximity to the patient.

It is a still further object of the invention to provide a method for optimal loosening and breakup of phlegm and mucus plugs in a patient's airways and lungs.

It is a still further object of the invention to provide an active acoustical apparatus that can automatically generate an acoustic waveform that approximates the frequency spectrum of a patient's breathing sounds to optimize breakup of phlegm and mucus plugs in the patient's airways.

It is another object of the invention to provide a powered apparatus which a patient can use while breathing in a normal manner and which automatically optimizes transmission of acoustic vibrations directly into a patient's airways based on monitoring of at least one physical parameter indicative of one or more body functions.

These and other objects and features of the invention are achieved by utilizing an electrically powered apparatus which produces an acoustic signal and directs the signal directly into a patient's airways. The acoustic signal may comprise a continuous tonal spectrum or noise spectrum, an intermittent acoustic spectrum, or series of sound pulses. The apparatus comprises a housing, a power supply, an acoustic generator preferably including a variable frequency oscillator and an audio amplifier in the housing connected to the power supply, an audio transducer such as a speaker connected to the amplifier and facing a biologic barrier such as an elastic diaphragm in the housing forming a portion of a sonic coupling air chamber in the housing, and a mouthpiece at one end of the housing connected to the air chamber. The mouthpiece is adapted to be held in a user's mouth while breathing during operation of the apparatus.

When the user closes his or her mouth around the mouthpiece of the apparatus, the mouthpiece forms a passage which directly couples the air chamber into the user's airways including the user's, i.e., patient's, bronchial tubes and lungs. The housing also has a breathing passage or series of ports preferably formed around and alongside the mouthpiece, or alternatively formed by a plurality of small holes through the peripheral wall of the air chamber in the housing. These passages permit the user's breath to exit the sonic coupling air chamber. The user draws fresh air for each breath into his or her lungs during operation of the apparatus through these breathing passages.

The breathing passages may be formed by one or more tubes or tubular passages coaxially extending alongside the central passage through the mouthpiece. These breathing passages may be integrally formed in the mouthpiece by a short annular sleeve formed around the central passage through the mouthpiece. The breathing passages have a total cross sectional area that is much smaller than the central passage through the air chamber and mouthpiece into the user's mouth, bronchial tubes and lungs. However, the breathing passage or passages cross sectional area is large enough to permit the user to breath at a normal rate without undue restriction.

The method in accordance with the present invention of loosening phlegm and mucus plugs in a patient's airways and lungs basically comprises the steps of:

generating an acoustic waveform such as a sequence of sonic pulses in an acoustic signal generator;

directing the waveform directly into the patient's airways while the patient breathes in and out;

sensing a signal representative of the patient's respiration such as the sound of the patient's breathing;

feeding the representative signal back to the acoustic signal generator; and adjusting a portion of the waveform generated by the acoustic signal generator to the representative signal to thereby approximate at least a portion of the sound of the patient's breathing.

More generally, the method of the invention comprises the steps of:

sensing a parameter representative of a patient's breathing efficiency such as breathing sounds or blood oxygen levels;

generating an acoustic waveform in an acoustic generator;

directing the waveform into the patient's airways while the patient breathes in and out; and adjusting the generated acoustic waveform to optimize the effect on the sensed parameter.

In the case of sensing the sound of a patient's breathing, the step of adjusting preferably may include matching at least a portion of the frequency spectrum of the sensed sounds of the patient's breathing in the acoustic generator such that the generated waveform closely corresponds to the sensed frequencies.

The first embodiment of the present invention is entirely manually adjusted. To operate the apparatus of the first embodiment of the invention, the user inserts the mouthpiece of the apparatus into his or her mouth and breathes normally, inhaling and exhaling through the breathing passages. The user turns on the apparatus and the transducer produces an acoustic waveform which may be a continuous waveform or a series of sonic pulses which are directed through the sonic air coupling chamber into the user's lungs through the central aperture in the mouthpiece. The apparatus includes controls for the user to vary the continuous or intermittent mode of operation, the amplitude, repetition rate, frequency and the frequency mixture of the transmitted sound waveform so that the user can manually select the particular optimum combination for his or her condition.

Another, second embodiment of the apparatus in accordance with the present invention further includes an automatic mode of operation, which utilizes an acoustic feedback circuit to the acoustic generator transmitting the sound pulses or sound spectra that is designed to optimize one or more monitored parameters. The feedback circuit includes a sensor for detecting and monitoring a parameter such as the pitch or frequency spectrum of sounds produced by the patient when exhaling and inhaling between active pulse emissions, when operating in the pulse mode. Blood oxygen level is another exemplary monitored parameter which is particularly suited for use when the apparatus is operated in the continuous waveform generating mode.

The feedback circuit preferably automatically compensates or adjusts the waveform, e.g., amplitude, frequency, frequency spectrum and/or repetition rate produced by the acoustic generator of the apparatus to optimize the effect on the parameter being monitored. This second embodiment may be switched by the user between manual and automatic modes of operation. This embodiment preferably utilizes an analog to digital converter (ADC) coupled to a microprocessor or digital signal processor (DSP) to provide the feedback signal from the user's monitored parameter to automatically adjust the generated waveform in order to optimize the monitored parameter.

One example involves monitoring the sound of the user's breathing. In this case, the transducer itself may be used, in between the pulses in pulse mode, as a listening sensor (microphone) to pick up and amplify the user's breathing sounds between periods of operation. When a digital signal processor is used, the transducer itself may be used even during waveform transmission, to listen to the user's breathing sounds by canceling out the transmitted waveform using digital sampling techniques. Alternatively, a separate microphone may be provided. The optimum result is provided, in the case of monitoring the sound of the patient's breathing, when the frequency spectrum produced by the apparatus substantially matches the spectrum of the user's breathing or wheezing sounds.

In the case where blood oxygen level is monitored, the optimum is provided when the monitored oxygen level is maximized. In this case, the DSP may include generation of a predetermined or preprogrammed sequence of frequency spectrums to be generated and tested to systematically determine where the maximum benefit on oxygen level is obtained.

Another example of a monitored parameter may be an ultrasonic monitor which senses an ultrasonic signature of a mucus plug. When a person has mucus plugs that restrict air passage, often an ultrasonic signature is produced by the patient's breathing around this plug. The presence of this ultrasonic signature can be used to trigger generation of an acoustic waveform search pattern. As the frequency of the acoustic waveform generated pattern approaches and then matches the resonance frequency of the mucus plug, the ultrasonic signature of the plug will change. This change is detected and signals to the acoustic generator that the resonant frequency, i.e. optimal frequency for mucus plug loosening, has been reached. The acoustic generator then reproduces the resonant frequency waveform to further loosen the mucus plug The apparatus in accordance with the present invention may be operated for as long as needed by the user. The user need only remove the mouthpiece while coughing to expel phlegm and mucus loosened by the vibrations of the generated waveform or sound pulses transmitted directly into the user's lungs.

Another unique feature of the present invention is that it is sound damped, i.e., virtually all of the sound produced by the acoustic transducer is directed through the air chamber into the user's bronchial tubes and lungs and not out through the walls of the apparatus. Therefore a user may utilize the apparatus in a crowded environment without disturbing others in the immediate vicinity. The cavity behind the acoustic transducer is filled with an absorptive material which dissipates resonances in the cavity behind the transducer and absorbs energy from the rear of the transducer to improve forward transmission efficiency.

The apparatus of the invention may be either battery powered by conventional batteries or may be powered from normal house current. The power supply in the apparatus may also include rechargeable batteries for use while traveling. These and other features and advantages will become more apparent from a reading of the following detailed description when taken in conjunction with the drawing figures.

DETAILED DESCRIPTION OF THE INVENTION

Figure 1:
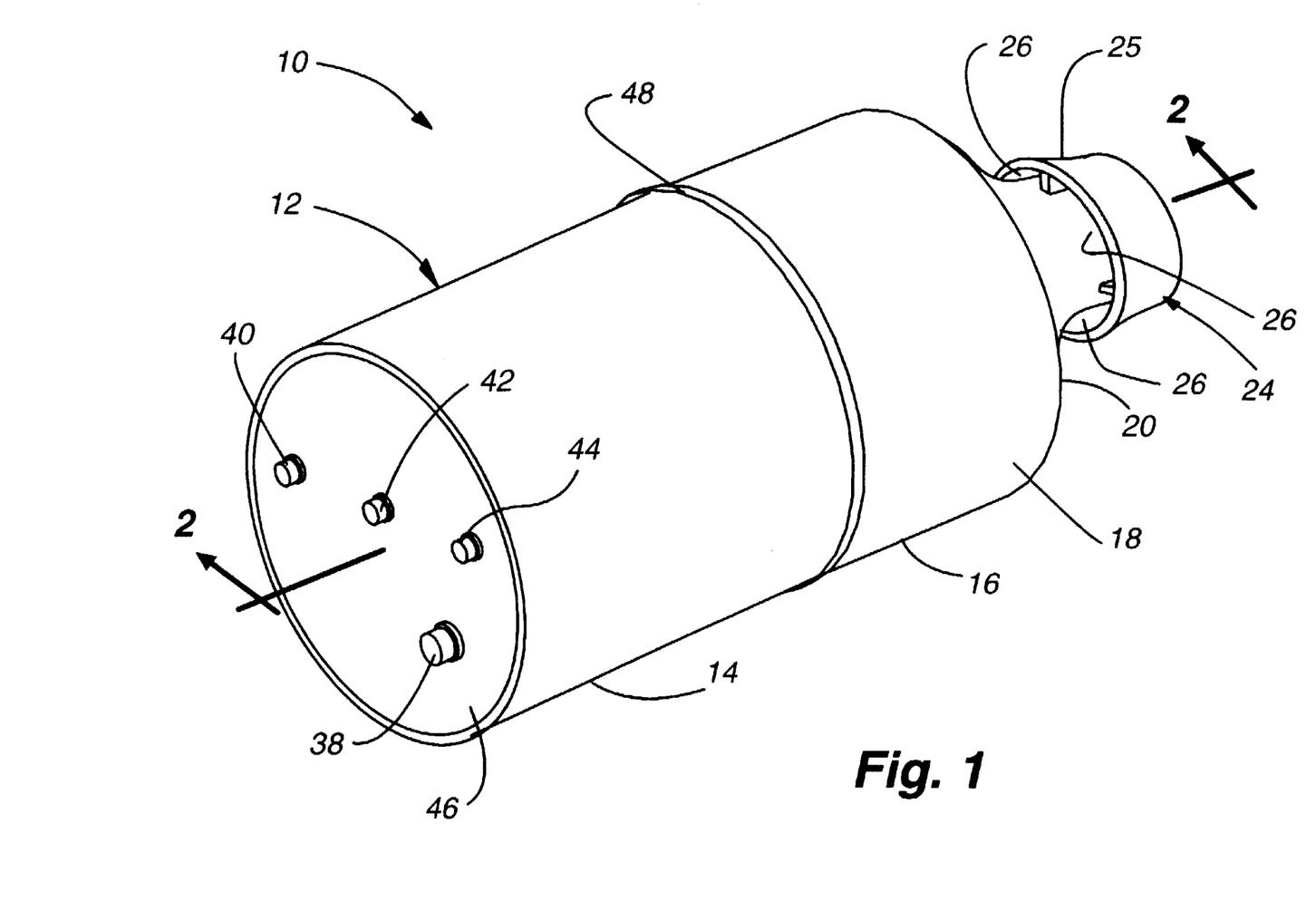
FIG. 1 is a perspective view of a first embodiment of the apparatus in accordance with the present invention.

Referring to FIG. 1, a first embodiment of an apparatus 10 in accordance with the present invention is shown in a perspective view. The apparatus 10 comprises a generally cylindrical housing 12 that has a bottom or base tubular portion 14 and a generally tubular cap portion 16. The cap portion 16 has a tubular side wall 18 and preferably a generally funnel shaped end wall 20 having a central aperture 22 therethrough connected to a preferably semi-rigid mouthpiece 24 designed to be held in the user's mouth between the teeth. The mouthpiece 24 preferably includes a peripheral sleeve 25 forming a plurality of breathing passages 26 extending alongside the body of the mouthpiece 24. An end view of the mouthpiece 24 is shown in FIG. 3A.

The peripheral sleeve 25 is spaced from the body of the mouthpiece 24 by axially extending ribs 27. These ribs 27 divide the annulus formed between the body of the mouthpiece 24 and the peripheral sleeve 25 into the plurality of tubular passages 26 which extend alongside the body of the mouthpiece 24 a sufficient distance, about an inch, so that the user does not cover their end openings with his or her lips. The breathing passages 26 allow the user to breath fresh air normally in and out through the mouth during operation of the apparatus 10. Although the passages are not required since the user can breathe through his or her nose, the passages are preferred since often a user may have constricted sinuses, a stuffy nose, etc. The width of the passages 26 shown in the FIGS. 1, 2, and 3A are shown exaggerated for clarity. In reality, the width is much narrower. The passages 26 have a total cross sectional area that is small compared to the area of the central aperture 22 through the mouthpiece 24 so that the sound transmitted through the central aperture 22 into the user's airways is not diverted out through the breathing passages 26.

Figures 2, 3A, 3B:
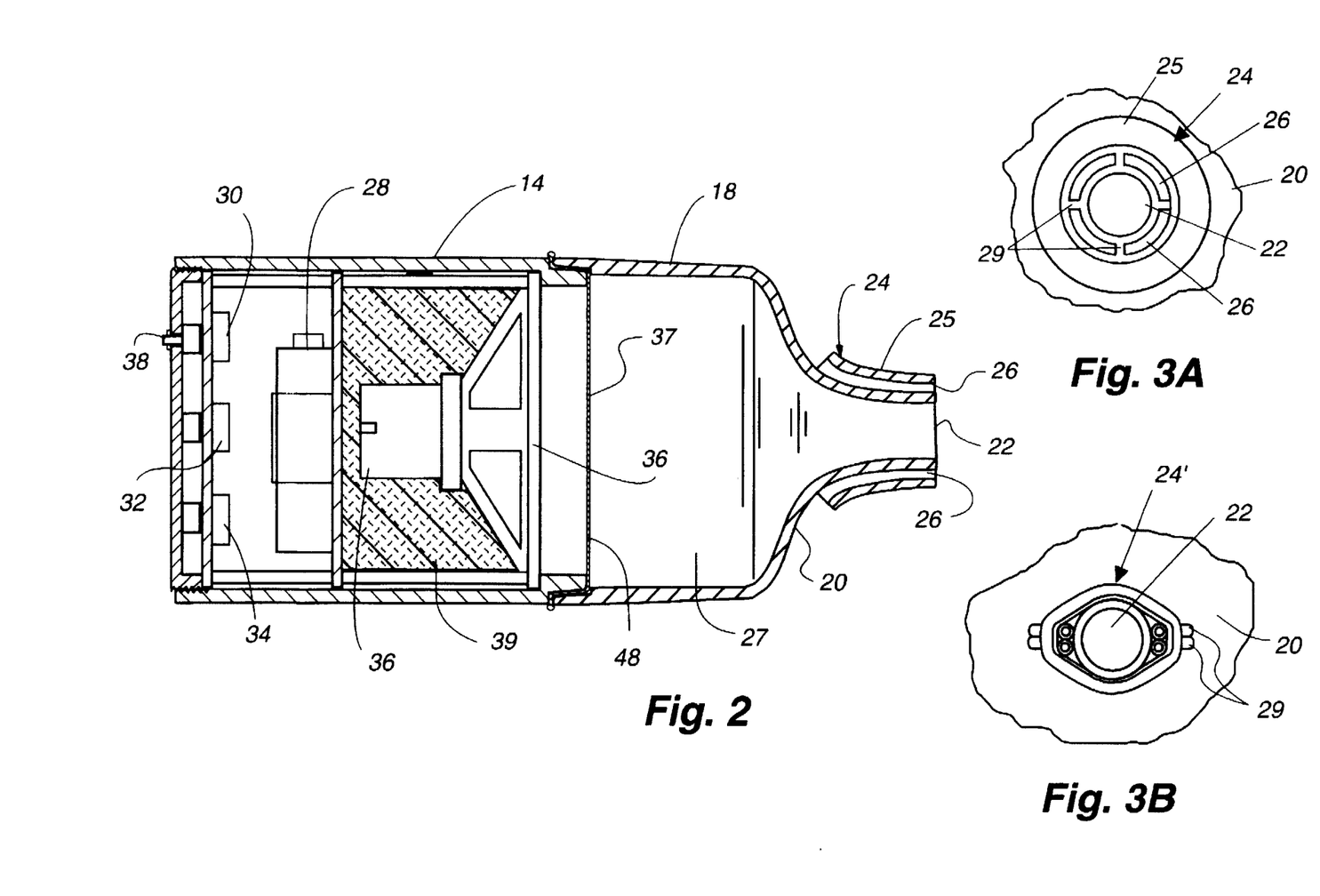
FIG. 2 is a sectional view of the apparatus in accordance with the present invention shown in FIG. 1.
FIG. 3A is an end view of the mouthpiece of the apparatus in accordance with the invention shown in FIG. 1.
FIG. 3B is an end view of an alternative mouthpiece of the apparatus shown in FIG. 1.

An alternative arrangement of the tubular passages 26 in the mouthpiece 24' is shown in FIG. 3B. In this embodiment, the breathing passages 26' are comprised of actual short tubes 29 extending axially alongside the body of the mouthpiece 24. These tubes 29 are banded together around the body of the mouthpiece 24 and may be removed and replaced as may be required for cleaning.

The bottom or base portion 24 of the apparatus 10 contains an acoustic generator which comprises a battery power supply 2$, a circuit board 30 containing an audio oscillator circuit 32 and an audio amplifier circuit 34 thereon, and supports an acoustic transducer 36 connected to the output of the audio amplifier 34. The transducer 36 is essentially a conventional speaker. As more fully described with reference to the second embodiment below, the transducer 36 may be a combination speaker/microphone which operates as a conventional speaker when electrically driven and as a microphone when acoustically driven by the patient's breathing sounds. An on/off/mode switch 38, volume control 40, frequency control 42, and a repetition rate control 44 are preferably accessible through apertures in a disk shaped bottom plate 46 closing the bottom or base of the tubular portion 14.

These four switches shown are exemplary and may be replaced by a different combination of switches with the functions designated by button sequences or combinations. For example, there may be only three buttons or switches 38, 40 and 462 In this case button 38 alone could turn the apparatus on or off and pressing switch 38 twice in succession could switch between pulse and continuous modes. Both switches 38 and 40 depressed together could increase the volume. Switch 40 alone could decrease the volume. Both switches 38 and 42 depressed together could increase the frequency and depressing switch 42 alone could decrease the frequency. Switches 40 and 42 depressed simultaneously could change repetition rate. Two switches may also be used. In this case, pressing both together once could turn the unit on. Pressing both together twice could switch between continuous and pulse modes. Pressing both together and holding for a predetermined period of time could turn the apparatus off. Pressing and holding one of the switches would increase the volume. Pressing and holding the other switch would increase the frequency. Pressing and holding the first switch again could decrease the volume, pressing both simultaneously could change to the repetition rate adjust mode and so on. Other combinations readily apparent to those skilled of the art may also be utilized and may easily be facilitated. The configuration shown is merely an illustrative example.

The base tubular portion 14 and the cap portion 16 are preferably telescopically mated together with a replaceable elastic diaphragm 48 captured therebetween, i.e., captured by the telescoping ends of the tubular portions 14 and 16. The purpose of the diaphragm 48 is primarily to prevent biological contaminants from reaching the transducer cone 37 and the electrical components in the lower portion 14 of the housing 12. Accordingly, the diaphragm 48 may be either reusable or disposable. Alternatively, the cap portion 16 and diaphragm 48 may be integrally made as a single disposable unit.

The cap portion 16, the diaphragm 48 over the cone 37 of the transducer 36, and the mouthpiece 24 together define an acoustic coupling chamber 27 which couples the transducer 36 to the user's airways when the mouthpiece 24 is held in a user's mouth. When the diaphragm 48 is provided as a separate piece, the diaphragm 40 is preferably stretched over the bottom end of the cap portion 16 during housing assembly and then the cap portion 16 is slipped over the open transducer end of the bottom portion 14. In this way, when the apparatus 10 is disassembled for cleaning after use, the cap portion 26, diaphragm 48, and mouthpiece 24 can be removed as an assembly. The component parts may then be cleaned and/or sterilized and the diaphragm 48 replaced as may be necessary.

Alternatively, the diaphragm 48 may be first installed over the cone 37 of the transducer 36 on the bottom portion 14 and/or the cap portion 16 may alternatively be sized to fit within the open end of the bottom portion 14. The cap portion 16 and base portion 14 may be also be constructed to be mated in any other conventional manner.

The diaphragm 48 may optionally be an annular disk of thin elastic material with a relatively rigid rim which fits snugly within either the cap portion 16 or within the bottom portion 14. The diaphragm 42 may also be designed to slip over one of the portions 14 or 16 with a semi rigid rim snap fitting within an external groove or internal groove in one of the portions (not shown). In any event, the diaphragm 48 is placed so as to shield the transducer cone 37 from any contaminants that may be exhaled by the user of the apparatus 10 of the invention but still transmit sound vibrations therethrough from the transducer 36 into the acoustic chamber 27 of the cap portion 16 and into the user's airways.

The mouthpiece 24 may be a separate piece physically attached to the exterior of the cap portion 16. In this case, the ribs 27 may frictionally grip or be adhesively bonded to the end wall 20 around the aperture 22. Alternatively, the cap portion 16 and the mouthpiece 24 may be formed as a one piece molded structure. In this instance, the inside surface of the cap portion 16 and mouthpiece 24, together with the cone of the transducer 36, define the coupling chamber 27. The mouthpiece 24 as shown in FIGS. 1, 2, and 3A may be either separately formed or may be integrally molded into the cap portion 16.

Since the diaphragm 48 is elastic, supple and flexible, its presence is virtually transparent to the sound transmission from the transducer 36 through the sonic coupling chamber 27 into the patient's airways during use. The transducer 36 is preferably sized so that the outer diameter of the cone 37 is approximately the same as the internal diameter of the tubular bottom portion 14. The transducer 36 nests in the tubular bottom portion 14 and the cone faces the cap portion 16 and the diaphragm 48. The transducer preferably is of a compact, high efficiency design so as to minimize power drain.

The space behind and around the rear of the transducer cone 37 in the base portion 14 of the housing 12 is preferably filled with a sound absorptive material 39. This sound dampening material 39 may be a fibrous batting such as cotton, etc. The purpose of this material 39 is to prevent substantive sound transmission outside of the base portion 14 of the housing 12 except forward through the sonic coupling chamber 27 and through the aperture 22 in the mouthpiece 24 into the patient's airways and lungs. Thus the material 39 dissipates resonances in the cavity behind the transducer cone and absorbs energy from the rear to increase forward sound transmission efficiency. However, the presence of this absorptive damping material has an adverse affect on power consumption. The amplifier output must be increased in order to overcome the drag on the cone 37. It is believed that the power output of the transducer 36 during operation as a speaker should thus preferably be within a range of around 5 to 7 watts in order to maintain efficiency and effectiveness of pulse delivery.

A patient breaths fresh air through the passages 26 around the aperture 22 while holding the mouthpiece 24 in his or her mouth. The continuous acoustic waveform or sound pulses emitted by the transducer 36 are focused through the aperture 22 directly into the patient's airways. Simultaneously, the patient breathes normally through the passages 26 which open to the air external to the chamber 27. Sound is substantially prevented from escaping the housing 12 when the continuous acoustic waveform or sonic pulses are being produced primarily because of the size of the passages 26 and the presence of the damping material 39 behind the transducer 36. Each of the mouthpiece passages 26 has an effective diameter that is much smaller than the predominant wavelengths of the sounds being generated by the transducer 36, on the order of less than 0.5 inch. For example, the wavelength of a 60 hertz sound is 18 feet. The wavelength of a 1000 hertz sound is 1.09 feet, and 10,000 hertz is 0.1 foot. The effective passage diameter for each passage is preferably on the order of 0.050 inches to 0.075 inches, or 0.004 feet, which is preferably at least an order of magnitude smaller than the wavelength of the sound being transmitted. The most effective frequencies of interest are believed to be less than 10,000 hertz. The apparatus 10 in accordance with the invention may, however, have any frequency range. A range between 10 hertz and 10,000 hertz is presently preferred.

Users will most likely utilize frequencies between 20 to 300 hertz, as these are the frequencies most often associated with phlegm vibration. For most frequencies of interest, the effective diameter of the breathing passages 26 is thus at least one to two orders of magnitude smaller than the wavelengths of the sounds produced. Since these passages 26 are substantially smaller than the wavelengths of interest, little sound pressure will be lost from the chamber 27 even when their combined effect is considered. However, these passages are important because they permit the user to breath substantially normally while using the apparatus 10.

The passages 26 may be located anywhere in or around the walls of the sonic coupling chamber 27. For example, they may alternatively be located in the side wall 18, the end wall 20, or around the mouthpiece 24. The mouthpiece 24 shown in FIGS. 1, 2, and 3A is preferred in the present invention. The size of the passages 26 may also be larger than described above, if other means of preventing substantial loss of acoustic pressure waves is provided. For example, the passages 26 may be partially covered by an integral baffle arrangement molded or otherwise formed within the mouthpiece 24 or the cap portion 16. Other sonic guide and focusing structures may also be provided within cap portion 16 to enhance the sonic pressure pulse transmission into the user's airways and lungs.

As stated above, the space behind the transducer cone 37 is substantially filled with sound damping material 39. The presence of this absorptive material and the lack of holes in the tubular wall of the base portion 14 to equalize pressure requires that net power delivered to the transducer 36 must be increased due to the drag this closed space provides on the transducer cone 37. However, this drag is small compared to the advantage of preventing unwanted noise projection outside of the housing 12. In addition, the damping material 39 increases the forward sound transmission efficiency. Thus, in operation, a person sitting or standing next to the user will barely detect any sound from the apparatus 10 while it is being used.

The space between the diaphragm 49 and the transducer 36 is a closed space. However, because the diaphragm 48 is very flexible and resilient, made of preferably a very elastic material such as latex or synthetic rubber, little acoustic attenuation results and the sound pulses effectively are transmitted through the diaphragm unimpeded from the transducer 36 through the coupling chamber 27. The cylindrical wall 18 of the cap portion 16 may optionally be shortened such that it is almost flush with the diaphragm 48. The shape of the end wall 20 may also be other than the funnel shape as shown.

Figure 4:
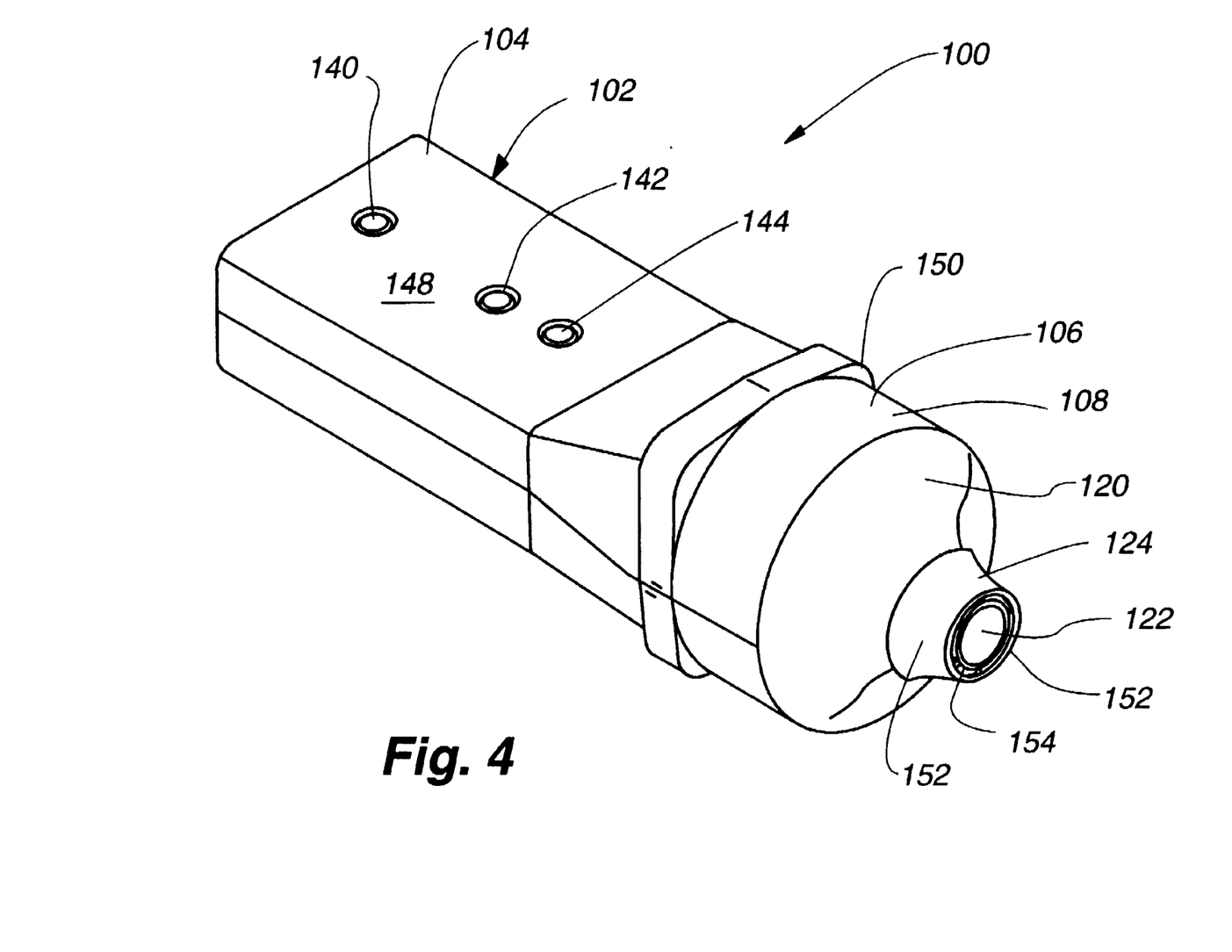
FIG. 4 is a perspective view of a second embodiment of the apparatus in accordance with the present invention.
Figure 5:
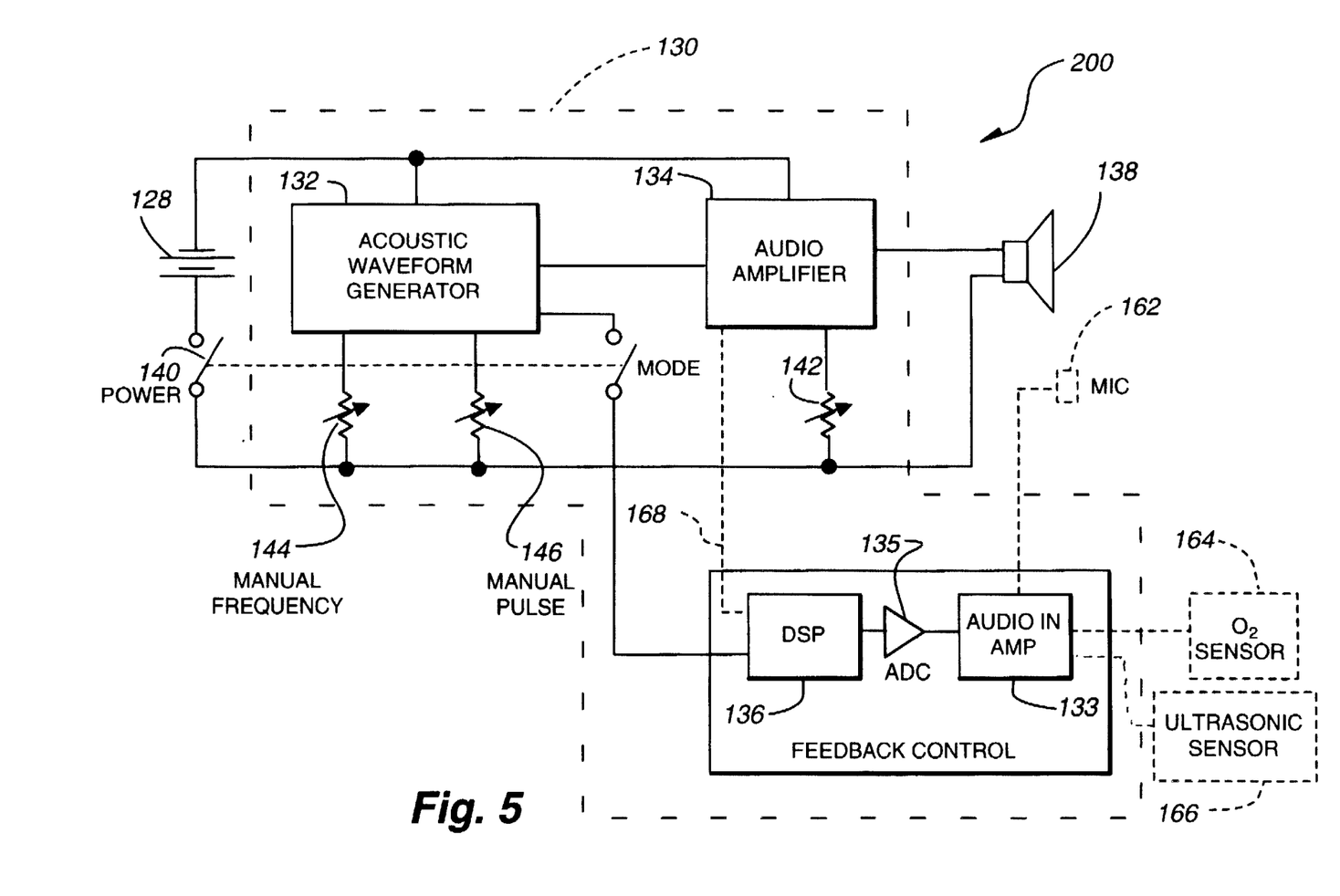
FIG. 5 is a schematic block diagram of the electrical circuit of the apparatus shown in FIG. 4.

A second embodiment 10 of the present invention is shown in FIGS. 4 and 5. This embodiment illustrates one alternative shape variant. The apparatus 100 comprises a hollow housing 12 that has a bottom or base portion 104 and a cap portion 106. The cap portion 106 has a tubular side wall 108 and a funnel shaped end wall 120 having a central aperture 122 and a semi-rigid mouthpiece 124 formed around the aperture 122 designed to be held in the user's mouth between the teeth.

The bottom or base portion 104 has a generally rectangular box portion containing a battery power supply 128 and an acoustic generator comprising a circuit board 130 containing an audio oscillator circuit 132, an audio in amplifier circuit 133, an audio amplifier circuit 134, an analog to digital converter 135, and a digital signal processor 136. The audio amplifiers 133 and 134 are connected to an audio transducer 138. An on/off/mode switch 140, volume control 142, and frequency control 144 are accessible through apertures in the wall 148 of the base portion 104. A repetition rate control 146 is actuated by pressing switches 142 and 144 simultaneously. The audio oscillator/waveform generator circuit 132 generates an acoustic waveform which may be continuous or broken into sonic pulse signals which are in turn fed to the audio amplifier 134 and then to the transducer 138 which generates the actual sounds.

The mating ends of the base portion 104 and the tubular cap portion 106 are preferably telescopically joined together as in the first embodiment described above. A replaceable elastic diaphragm 150 is preferably captured between the telescoping ends of the tubular portions 104 and 106. The purpose of the diaphragm 150 is again to act as a biological shield primarily to prevent contaminants from reaching components in the lower tubular portion 104 of the housing 102. Accordingly, the diaphragm 150 may be reusable or disposable. Alternatively, the diaphragm 150 may be integrally formed with the cap portion 106 so as to be disposable as a unit. The cap portion 106, the cone of the transducer 138, and the mouthpiece 124 together define an acoustic coupling chamber 127 which couples the transducer 138 to the user's airways when the apparatus 100 is placed in a user's mouth.

In the embodiment shown in FIGS. 4 and 5, the diaphragm 150 is preferably stretched over the bottom end of the cap portion 106 and then the cap portion 106 is slipped over the open transducer end of the bottom portion 104. In this way, when the apparatus is disassembled after use, the cap portion 106, diaphragm 150, and mouthpiece 124 are removed as an assembly. The component parts may then be disassembled, cleaned or sterilized, or replaced as in the first embodiment discussed above.

Alternatively, the diaphragm 150 may be first installed on the bottom portion 104 and/or the cap portion 106 may alternatively be sized to fit within the open end of the bottom portion 104. The diaphragm 150 may optionally be an annular disk of thin elastic material with a relatively rigid rim which fits snugly within either the cap portion or the bottom portion 104. In any event, the diaphragm 148 is placed so as to shield the transducer cone from any contaminants that may be exhaled by the user of the apparatus of the invention but still transmit sound vibrations therethrough into the cap portion 106.

Preferably the mouthpiece 126 is integrally formed with the cap portion 106 as a one piece molded structure. In this instance, the cap portion 106 and mouthpiece 126, together with the cone of the transducer 136, define the coupling chamber 127. Since the diaphragm 150 is elastic, supple and flexible, its presence is virtually transparent to the sound transmission from the transducer 136 through the sonic coupling chamber 127 into the patient's airways during use. The mouthpiece 126, the cap portion 106 and the diaphragm 150 may be manufactured as a disposable self contained unit rather than being separable into its component parts.

The transducer 138 is preferably sized so that the outer diameter of the vibrating cone is approximately the same as the internal diameter of the tubular cap portion 106. The transducer 136 preferably nests in the tubular bottom portion 104 and the cone faces the cap portion 106 and the diaphragm 150 as in the first embodiment. The transducer 138 preferably is of a compact, high efficiency design so as to minimize power drain. The power output of the transducer in this embodiment is generally similar to that of the first embodiment. Thus the effective power output should preferably be in the range of 5 to 7 watts for the same reasons. This power limitation may optionally be designed into the amplifier circuitry to preclude inadvertent over stimulation of sensitive lung tissues.

The bottom portion 104 differs from the first embodiment primarily in that it includes a closed rectangular part to house the power supply 128 and printed circuit board 130. This rectangular part of the bottom portion 104 may be a clam shell design that snaps closed. The front part of the bottom portion 104 is shaped to closely enclose the transducer 138. The portion 104 behind the transducer cone is again filled with a sound absorbing material such as cotton batting or foam as in the first embodiment 10. This configuration eliminates or reduces substantially the sound transmitted outside the apparatus 100 during operation of the device. Consequently, power to the transducer or other acoustic transducer 136 must be increased as discussed above to compensate for the power lost in overcoming the damping effect of this closed and at least partially filled volume behind the transducer cone. The space between the diaphragm 150 and the front face of the transducer 136 is also a closed space. However, because the diaphragm 150 is very flexible and resilient, made of preferably a very elastic material such as latex or synthetic rubber, little acoustic attenuation results and the sound pulses effectively are transmitted by the transducer cone through the diaphragm unimpeded from the transducer 136 through the coupling chamber 127. Again, one major advantage of this second embodiment is that the apparatus 100 is very quiet to operate and may be operated by a patient in close proximity to other people without substantially interfering with their activities.

The funnel shaped tubular side wall of the cap portion 106 is solid and smoothly curves into the mouthpiece 124. In order for the user to breathe through the sonic coupling chamber 127 while using the apparatus 100 in accordance with this embodiment of the present invention, one or more passages is formed by a segmented annular sleeve 152 supported by and integral with the mouthpiece 124. This sleeve 152 forms a plurality of coaxial passages 154 around the mouthpiece 124 as in the first embodiment which together form a large enough passage to the outside environment for the patient to breath through. Each of the passages 154 has a width of between $\frac{1}{16}$ to about $\frac{1}{8}$ inch. Each passage 154 width is much smaller than the wavelength of the sounds being generated by the transducer 136. Since the widths are substantially smaller than the acoustic wavelengths of interest, little sound pressure will be lost from the chamber 127 even when their combined effect is considered.

The bottom portion 104 differs from the first embodiment 10 in that not only does it have a closed volume behind the transducer 138, the transducer 138 preferably operates as a microphone between active pulses, i.e., between transmitted bursts of sound. The transducer 138 acts as a microphone to produce electrical signals representative of the patient's breathing sounds and feeds these signals to the amplifier circuit 200 shown in FIG. 5.

It has been found that when a patient's lungs are stimulated with a sound spectrum that substantially corresponds to the sound of the patient's wheezing, the phlegm causing the wheezing sound is specifically targeted and loosened. It appears that the wheeze sound may be substantially the resonant frequencies of the phlegm and mucus plugs. Consequently, if the resonant frequencies can be sensed and duplicated or targeted, dislodging the phlegm and mucus plugs almost immediately ensues. Therefore, this second embodiment 100 of the apparatus of the invention includes an automatic tone generation/adjustment feature.

In addition to having the manually variable pitch and duration controls as described above with reference to the first embodiment, this second embodiment 100 includes a feedback function which senses a parameter indicative of a user's breathing efficiency and uses the sensed parameter to automatically adjust the output acoustic waveform to optimize the device's affect on the monitored parameter. The monitored parameter, in the illustrated second embodiment, is preferably the sound produced by the user during breathing. This second embodiment 100 includes an audio in amplifier 133 connected to the transducer 138 which receives and amplifies sound signals received from the transducer 138, for example, in the pulse mode, when the transducer is between pulses, i.e. when the transducer 138 is "listening". The audio amplifier 133 is connected to the ADC 135 which is in turn connected to the DSP 136. The DSP 136 is connected through the off/on/mode switch 140 to the acoustic waveform generator 132.

Alternatively, the DSP 136 may be used to digitally directly generate the acoustic waveform. In this instance it may be connected directly to the audio amplifier 134 as shown by the dashed line 168 in FIG. 5. The DSP 136 may be utilized to detect the sound of a patient's breathing even during transmission of the acoustic waveform to the user via digital sampling techniques to cancel out the transmitted waveform, which unmasks the user's breathing sounds.

During or between pulses, and preferably whenever the apparatus 100 is on but not generating an acoustic waveform, the transducer 138 senses the patient's breathing sounds. The DSP 136 processes these sound signals and produces a feedback signal to the oscillator/pulse generator 132 to produce an output sonic waveform that closely matches in frequencies the respiration sound from the patient. This automatic frequency adjustment or matching may be turned on and off by the user/patient preferably via operation of the switch The apparatus 100 may alternatively utilize a separate microphone 162, as shown dotted in FIG. 5, rather than the transducer 130. In addition, the embodiment 100 may include detection of separate parameters which may have a bearing on the success of the therapeutic apparatus of the present invention. For example, the input amplifier 133 or the signal processor 136 may be connected to an external parameter sensor such as a blood oxygen sensor 164 or an ultrasonic sensor 166. In the former instance, the volume, pitch and/or frequency spectrum output of the transducer 138 may be optimized to achieve maximum blood oxygen levels. In this case, the frequencies and pulse durations produced by the apparatus 100 would be varied by the signal processor 136 in a predetermined pattern or sequence until the optimum level of oxygen is sensed.

Similarly, if an ultrasonic sensor is utilized, the sensor 166 may be utilized to first identify any signatures of mucus plugs present in the user's lungs via "listening" to the user's breathing sounds; second, initiating generation of a predetermined "hunting" sequence of acoustic waveforms and then third, monitoring the mucus plug signatures to detect a change in the signature during the hunting sequence. Such a change in mucus plug signature is believed to occur when the generated waveform closely matches to the resonant frequency or frequencies of the mucus plug. Finally, the sensed change in ultrasound signature is used to cause the acoustic generator to stop the predetermined sequence and reproduce the waveform that caused the signature change until the plug is loosened and the user coughs up the mucus plug. This hunting process may then be repeated until no further ultrasonic signatures or signature changes are detected.

The major advantage of this second embodiment is that it can automatically "zero in" on the resonant frequencies of the obstructions to efficient breathing and thereby optimize efficient loosening of mucus plugs and phlegm. Further, the apparatus 100 is very quiet to operate and may be operated without the patient consciously monitoring and manipulating its operation. In addition, it may be operated by the patient in close proximity to other people without substantially interfering with their activities.

The embodiments 10 and 100 may be constructed otherwise than as specifically disclosed above and shown with a reference to examples of preferred embodiments of the invention. Many changes, alterations and modifications may be made without departing from the scope of the invention. For example, the apparatus 10 is shown in a generally cylindrical housing. Other shapes may be utilized as well such as the combination shown in FIG. 4. The housing may also be telescopically expandable to provide an optimum coupling volume in a particular application or the housing may have an oval cross section or other cross sectional shape. A telescopically adjustable cap portion 16 with respect to base portion 14 would permit the sonic coupling chamber 27 to be tuned to various resonant frequencies in order to achieve optimum sonic pressure pulse delivery to the patient. The mouthpiece 24, end wall 22 and side wall 18 may be molded as an integral single unit. The bottom portion 14 may be much more compactly arranged and all components may be packaged with a rechargeable power supply rather than a battery pack or line cord. Also, the base portion 14 may include an integral pistol grip or other ergonomically desirable shape for the user to grasp during use. Accordingly, the invention is intended to encompass all such variations as will be readily apparent to those skilled in the art and is not limited to the embodiment shown and described above.

What is claimed is:

1. An apparatus for assisting a user in loosening phlegm and mucus plugs accumulated in a user's airways including bronchial tubes and lungs comprising:

an acoustic generator adapted to be coupled into said patient's mouth and thereby into a patient's bronchial tubes and lungs, said generator producing a sonic waveform during a first period of time while a user is breathing through a user's mouth;

an acoustic receiver coupled to a user's airways for sensing a breathing sound produced by a user during a second period of time; and a feedback control coupled to said receiver and to said acoustic generator for controlling said produced waveform so as to substantially match at least one frequency of said sensed breathing sound.

2. The apparatus according to claim 1 wherein said acoustic receiver is a microphone.

3. An apparatus for assisting a patient in loosening phlegm and mucus plugs accumulated in a patient's airways including bronchial tubes and lungs so that said phlegm and mucus plugs can be more readily expelled by a patient thereby improving a patient's breathing efficiency, said apparatus comprising:

an acoustic generator adapted to be coupled into a patient's mouth and thereby convey sound into a patient's bronchial tubes and lungs, said generator producing a sonic waveform while said patient is breathing through a patient's mouth;

a sensor connected to said patient for monitoring one or more parameters indicative of a patient's breathing efficiency; and a feedback control coupled to said sensor and to said acoustic generator for controlling and modifying at least a portion of said generated waveform so as to maximize a patient's breathing efficiency.

4. The apparatus according to claim 3 wherein said sensor is a microphone coupled into a patient's mouth.

5. The apparatus according to claim 3 wherein said sensor is a blood oxygen level monitor.

6. The apparatus according to claim 3 wherein said acoustic generator comprises:

a hollow housing having a cap portion and a base portion, said cap portion forming at least part of an acoustic coupling chamber, said cap portion having a mouthpiece around a portion of said chamber having at least one breathing passage therethrough leading out of said cap portion;

an audio signal generator housed within said base portion having an acoustic transducer coupled to said cap portion, said generator transmitting sonic pressure pulses into said coupling chamber; and said mouthpiece coupling the acoustic coupling chamber into a patient's airways when the mouthpiece is held in a patient's mouth and permitting a patient to breathe through the breathing passage while said coupling chamber directs said acoustic waveform from said acoustic transducer into a patient's airways.

7. An apparatus for assisting a patient in loosening phlegm and mucus collected in a patient's lungs, bronchial and/or tracheal passages comprising:

a hollow housing having a cap portion and a base portion, said cap portion forming at least part of an acoustic coupling chamber said cap portion having a mouthpiece around a portion of said chamber having at least one breathing passage therethrough leading out of said cap portion;

an audio signal generator housed within said base portion having an acoustic transducer coupled to said cap portion, said generator transmitting sonic pressure pulses into said coupling chamber;

said mouthpiece coupling the acoustic coupling chamber into a patient's airways when the mouthpiece is held in a patient's mouth and permitting a patient to breathe through the breathing passage while said coupling chamber directs said pressure pulses from said acoustic transducer into a patient's airways;

a microphone in said housing for receiving acoustic signals through said coupling chamber from a patient's airways; and a feedback control connected to said microphone and to said audio generator for controlling the frequency of said sonic pressure pulses.

8. The apparatus according to claim 7 wherein said feedback control controls said sonic pressure pulses to substantially match generated frequencies with the frequencies of said received acoustic signals from a patient's breathing through said airways.

9. An apparatus for assisting a patient in loosening phlegm and mucus collected in a patient's lungs, bronchial and/or tracheal passages comprising:

a hollow housing having a cap portion and a base portion, said cap portion forming at least part of an acoustic coupling chamber, said cap portion having a mouthpiece around a portion of said chamber having at least one breathing passage therethrough leading out of said cap portion;

an audio signal generator housed within said base portion having an acoustic transducer coupled to said cap portion, said generator transmitting sonic pressure pulses into said coupling chamber;

said mouthpiece coupling the acoustic coupling chamber into a patient's airways when the mouthpiece is held in a patient's mouth and permitting a patient to breathe through the breathing passage while said coupling chamber directs said pressure pulses from said acoustic transducer into a patient's airways; and a feedback control in said housing adapted to automatically adjust at least the oscillator frequency to optimize a parameter sensed from a patient.

10. The apparatus according to claim 9 wherein said parameter is the sound of a patient's breathing.

11. The apparatus according to claim 10 wherein the sound pulse generated by said acoustic generator is matched at at least one frequency to at least one frequency in the sound of a patient's breathing.

12. The apparatus according to claim 9 wherein said parameter is blood oxygen level.

13. The apparatus according to claim 12 wherein said feedback control adjusts generated sound pulses to maximize a patient's blood oxygen level.

14. An apparatus for assisting a patient in loosening phlegm collected in a patient's lungs and bronchial or tracheal passages comprising:

a hollow housing having a cap portion and a base portion, said cap portion forming at least part of a sonic coupling chamber, said cap potion having a central aperture and at least one breathing passage leading out of said acoustic coupling chamber and out of said cap portion;

said cap portion including a mouthpiece adapted to be held in a patient's mouth, said mouthpiece forming a part of the acoustic coupling chamber, said mouthpiece coupling the acoustic coupling chamber into a patient's airways, said mouthpiece permitting a patient to breath through the breathing passage while said coupling chamber directs said pressure pulses into a patient's airways; and an audio signal generator housed within said base portion having an acoustic transducer coupled to said cap portion, said generator transmitting sonic pressure pulses into said coupling chamber, said generator including a feedback means for sensing a parameter from a patient, processing said sensed parameter, and modifying said transmitted sonic pulses to optimize said parameter.

15. The apparatus according to claim 14 wherein said feedback means comprises a sensor adapted to detect blood oxygen levels in a patient.

16. The apparatus according to claim 14 wherein said feedback means comprises said transducer sensing a patient's breathing sounds.

17. The apparatus according to claim 16 wherein said feedback means further comprises a signal processor receiving said sounds, said signal processor automatically controlling generation of a frequency spectrum of said transmitted pulses to substantially match a frequency spectrum of a patient's breathing sounds.

18. The apparatus according to claim 14 wherein said feedback means comprises a separate acoustic transducer sensing a patient's breathing sounds in between emission of said sonic pulses.

19. The apparatus according to claim 18 wherein said separate transducer is a microphone.

20. The apparatus according to claim 14 wherein said audio generator is user selectable between at least two feedback input sensors.

21. An apparatus for assisting a patient in loosening phlegm collected in a patient's lungs and bronchial passages comprising:

a hollow housing having a separable cap portion and a separable base portion having a flexible sanitary diaphragm therebetween separating said base portion from said cap portion, said base portion containing an audio pulse generator therein connected to an audio transducer and a feedback control connected to said audio pulse generator, said cap portion having a mouthpiece and a central aperture therein, said cap portion forming at least a portion of a sonic coupling chamber adapted to be coupled to a patient's bronchial passages when said mouthpiece is held in a patient's mouth;

wherein said audio generator transmits an acoustic waveform into a patient's airways during a first time period and said feedback control, during a second time period senses acoustic waveforms produced by a patient through a patient's airways.

22. The apparatus according to claim 21 wherein said feedback control receives said sensed acoustic waveforms and controls said audio generator to substantially reproduce said sensed acoustic waveforms for transmission into said patient's airways.

23. The apparatus according to claim 22 wherein said feedback control controls the audio generator to substantially duplicate the frequency spectrum of said sensed waveforms for retransmission back into a patient's airways.

24. The apparatus according to claim 23 further comprising at least one additional sensor in addition to said transducer for detecting a parameter characteristic of a patient's respiration connected to said feedback control.

25. An apparatus for assisting a patient in loosening phlegm collected in a patient's lungs and bronchial passages comprising:

a hollow housing having a separable cap portion and a separable base portion, said cap portion having a mouthpiece around a central aperture adapted to be held in a patient's mouth and having a breathing passage therethrough out of said cap portion;

an audio signal generator in said base portion comprising an audio frequency oscillator, a signal processor and an amplifier connected to an acoustic transducer, said audio generator being separated from said cap portion by a replaceable flexible diaphragm, said cap portion, said diaphragm and said mouthpiece forming an acoustic coupling chamber into a patients mouth and airways through the central aperture, said generator being operable to send an acoustic pulse having a first frequency spectrum through said acoustic coupling chamber into a patient's airways during a first period of time, receive an acoustic signal having a second frequency spectrum through said coupling chamber from a patient's airways during a second period of time, and adjust a subsequent acoustic pulse to have a frequency spectrum substantially matching said second frequency spectrum from a patient's airways.

26. A method of loosening mucus plugs and phlegm in a patient's airways and lungs so that the patient can expel them, said method comprising the steps of:

generating an acoustic waveform in an audio signal generator;

directing the waveform directly into the patient's airways while the patient breathes in and out;

sensing a sound of the patient's breathing and producing a signal representative thereof;

feeding the representative signal back to the audio signal generator; and matching at least a portion of the generated waveform to the sensed sound of the patient's breathing.

27. The method according to claim 26 wherein said step of matching comprises passing said representative breathing signal through an analog to digital converter and then through a digital signal processor into said audio generator so as to control generation of said acoustic waveform.

28. The method according to claim 27 wherein said step of matching is automatically performed during operation of said apparatus.

29. The method according to claim 27 wherein said step of matching produces at least one acoustic frequency that resonates with a resonant frequency of one of said mucus plugs.

30. A method of optimizing loosening of a mucus plug in a user's airways including bronchial tubes and/or lungs so that the user can expel the mucus plugs and phlegm, said method comprising determining a resonant frequency of the mucus plug, generating an acoustic waveform including at least said resonant frequency, and applying said waveform directly into the user's airways while the user breathes through the user's airways.

31. The method according to claim 30 wherein said step of determining includes listening to the sound of the user's breathing.

32. The method according to claim 30 wherein said step of determining comprises applying a predetermined acoustic waveform sequence into the user's airways while the user breathes through the user's airways and monitoring a parameter indicative of the user's breathing.

* * * * *